(12) United States Patent
Hill (10) Patent No.: US 6,532,956 B2
(45) Date of Patent: Mar. 18, 2003

(54) PARAMETER VARIATION FOR PROPORTIONAL ASSIST VENTILATION OR PROPORTIONAL POSITIVE AIRWAY PRESSURE SUPPORT DEVICES

(75) Inventor: Peter D. Hill, Monroeville, PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/813,189

(22) Filed: Mar. 20, 2001

(65) Prior Publication Data

US 2001/0035186 A1 Nov. 1, 2001

Related U.S. Application Data

(60) Provisional application No. 60/193,200, filed on Mar. 30, 2000.

(51) Int. Cl.$^7$ ............................................. A61M 16/00
(52) U.S. Cl. .............................. 128/204.18; 128/204.23
(58) Field of Search ..................... 128/204.18, 204.21, 128/204.23, 204.26; 600/529, 533, 538

(56) References Cited

U.S. PATENT DOCUMENTS

| | | | |
|---|---|---|---|
| 5,044,362 A | | 9/1991 | Younes |
| 5,107,830 A | | 4/1992 | Younes |
| 5,535,738 A | | 7/1996 | Estes et al. |
| 5,694,923 A | * | 12/1997 | Hete et al. ............. 128/204.18 |
| 5,735,267 A | * | 4/1998 | Tobia .................... 128/204.18 |
| 5,794,615 A | | 8/1998 | Estes |
| 5,868,133 A | * | 2/1999 | DeVries et al. ........ 128/204.18 |
| 5,884,622 A | | 3/1999 | Younes |
| 6,000,397 A | * | 12/1999 | Skog .................... 128/203.12 |
| 6,024,089 A | * | 2/2000 | Wallace et al. ........ 128/204.21 |
| 6,041,780 A | * | 3/2000 | Richard et al. ........ 128/204.18 |
| 6,105,575 A | * | 8/2000 | Estes et al. ............ 128/204.21 |
| 6,152,129 A | * | 11/2000 | Berthon-Jones ........ 128/200.24 |
| 6,257,234 B1 | * | 7/2001 | Sun ....................... 128/204.18 |
| 6,302,105 B1 | * | 10/2001 | Wickham et al. ...... 128/204.18 |
| 6,302,851 B1 | * | 10/2001 | Gedeon ...................... 600/529 |
| 6,345,619 B1 | * | 2/2002 | Finn ..................... 128/204.21 |
| 6,360,745 B1 | * | 3/2002 | Wallace et al. ........ 128/203.12 |

* cited by examiner

*Primary Examiner*—Aaron J. Lewis
*Assistant Examiner*—Teena Mitchell
(74) *Attorney, Agent, or Firm*—Michael W. Haas (57) ABSTRACT

A system and method for providing a pressure support therapy administered to a patient, where at least one parameter associated with the pressure support therapy is varied according to a time-base parameter variation function. More specifically, at least one parameter or at least one group of parameters associated with a pressure control relation for providing a proportional assist ventilation (PAV) or a proportional positive airway pressure (PPAP) mode of ventilation is varied according to a time-based parameter variation function to control the PAV or PPAP ventilation with a maximum degree of flexibility.

10 Claims, 3 Drawing Sheets

PARAMETER VARIATION FOR PROPORTIONAL ASSIST VENTILATION OR PROPORTIONAL POSITIVE AIRWAY PRESSURE SUPPORT DEVICES

CROSS-REFERENCES TO RELATED APPLICATIONS

This application claims priority under 35 U.S.C. §119(e) from provisional U.S. patent application No. 60/193,200 filed Mar. 30, 2000.

BACKGROUND OF THE INVENTION

1. Field of the Invention

The present invention pertains to a pressure support apparatus and method for controlling a pressure support therapy administered to a patient, and, in particular, to a controlling a proportional assist ventilation or a proportional positive airway pressure mode of ventilating a patient by varying at least one parameter associated with one of these ventilation techniques according to a parameter variation function.

2. Description of the Related Art

It known to administer a therapeutic treatment to a patient in order to treat a breathing disorder or to provide a patient with life support ventilation via a ventilator or pressure support device. There are a variety of techniques for providing the flow of breathing gas to the patient, commonly referred to as modes of ventilation. Two such conventional modes of ventilation are proportional assist ventilation (PAV®) and proportional positive airway pressure (PPAP) ventilation.

PAV is taught by U.S. Pat. Nos. 5,044,362 and 5,107,830 both to Younes et al., the contents of which are incorporated herein by reference. According to this technique, the pressure delivered by the ventilator to the patient increases in direct proportion to patient breathing effort, so that the greater the patient effort, the greater the pressure of breathing delivered by the ventilator. More specifically, the pressure of gas delivered by the ventilator to the patient is determined based on a product of a first gain and a signal indicative of a rate of flow of breathing gas provided to such a patient in combination with a product of a second gain and signal indicative of a volume of breathing gas provided to the patient. This relationship is summarized as follows:

$$P_{patient} = FA * \dot{V} + VA * V, \quad (1)$$

where $P_{patient}$ is the pressure at the patient interface device, such as the patient's nasal mask, nasal/oral mask, nasal cannula, or trachea tube, FA is a flow assist multiplier, which is a fraction of respiratory resistance, $\dot{V}$ is the instantaneous flow of gas to the patient, VA is a volume assist multiplier, which is a fraction of respiratory elastance, and V is the instantaneous volume of gas delivered to the patient.

In a slight variant of the above-described PAV mode, pressure support is provided to a patient according to the following equation:

$$P_{patient} = \% \text{ Set } (FA * \dot{V} + VA * V) + EPAP, \quad (2)$$

where %Set is a common multiplier or scaling factor applied to both $FA * \dot{V}$ and $VA * V$, and EPAP is the expiratory positive airway pressure, which is a minimum baseline pressure applied to the patient during the expiratory phase of his or her breathing cycle.

In order to provide a patient with PAV as a mode of pressure support therapy or as a mode of ventilation, the caregiver sets the following parameters of equations (1) or (2): %Set, FA, VA, and EPAP. This is done either based on data garnered from patient observation and caregiver experience and expertise, data gathered from measurements of various physiological parameters of the patient, such as respiratory elastance and resistance, or based on a predetermined values that are generally believed to be appropriate for a given group of patients. Once the patient begins receiving PAV, he or she continues to receive PAV at the initially set parameters until the caregiver alters the parameters. For example, as the patient's physical condition improves he or she may need less assistance from the ventilator, so the caregiver may reduce the %Set level to reduce the assistance to breathing provided by the ventilator. It is also known to set one of more of the parameters, %Set, FA, VA, and EPAP, automatically, to modify these settings automatically, or both.

PPAP ventilation is taught by U.S. Pat. Nos. 5,535,738 and 5,794,615 both to Estes et al., the contents of which are incorporated herein by reference. According to this technique, the pressure of gas provided to the patient is a function of the patient flow rate. This relationship can be summarized as follows:

$$P_{patient} = P_{base} + \text{Gain} * \dot{V}, \quad (3)$$

where $P_{patient}$ is the pressure delivered to the patient interface device, $P_{base}$ is the base line pressure (greater than or equal to zero and conceptually equal to EPAP), $\dot{V}$ is the instantaneous flow of gas to the patient, which can be measured directly via a flow transducer or estimated from a flow transducer measurement and a leak component determination, and Gain is a constant used to augment the pressure delivered to the patient based on the flow rate.

In a variation of the PPAP ventilation technique, the pressure delivered to the patient is described according to the following functions:

$$P_{patient(insp)} = P_{base} + Gain_{insp} * Flow, \quad \text{and} \quad (4)$$

$$P_{patient(exp)} = P_{base} + Gain_{exp} * Flow, \quad (5)$$

where $P_{patient(insp)}$ is the pressured delivered to the patient during inhalation, $Gain_{insp}$ is the constant used during inspiration to boost pressure based on the flow rate, $P_{patient(exp)}$ is the pressure delivered during exhalation, and $Gain_{exp}$ is the constant used during exhalation to reduce pressure based on the flow rate.

As with PAV, the PPAP parameters, i.e., $P_{base}$, $Gain_{insp}$, and $Gain_{exp}$, of the PPAP relation are set by the caregiver and do not change unless altered by the caregiver. For example, the caregiver may deem it appropriate to change the $Gain_{insp}$ or $Gain_{exp}$ to maximize the comfort of the PPAP ventilation provided to the patient. It is also known to automate the process for setting the PPAP parameters automatically, automate the process for modifying these parameters, or to automate both the initial setting and modification of these parameters.

Regardless of whether the patient is provided with PAV or PPAP ventilation, conventional ventilation techniques involve starting the patient on either pressure support therapy by setting the various parameters and then starting the therapy. The patient is left to cope with the relatively sudden change in ventilation assistance once the ventilation assistance begins. Depending on the amount of assistance provided by the PAV or PPAP mode, this transition can be relatively large. Of course, the caregiver can manually adjust the parameters to provide a more comfortable transition for the patient. However, this requires the caregiver continually monitor and manually change the ventilator settings, which is time consuming. Likewise, when a patient is being weaned off of a ventilator, unless the caregiver manually, incrementally decreases the ventilation assistance provided by the PAV or PPAP mode of ventilation, the patient is forced to cope with the relative abrupt transition from receiving ventilation assisted breathing to receiving no such assistance.

SUMMARY OF THE INVENTION

Accordingly, it is an object of the present invention to provide a patient treatment system that overcomes the shortcomings of conventional patient treatment systems employing the PAV or PPAP ventilation mode This object is achieved according to one embodiment of the present invention by providing a patient treatment system that includes a gas flow generating system, a pressure controller, and a flow and volume sensing system. The gas flow generating system provides a flow of breathing gas to an airway of a patient. The pressure controller controls the pressure of breathing gas provided to the patient. The sensing system for detects the instantaneous flow rate $\dot{V}$ and instantaneous volume V of breathing gas provided to the patient. The patient treatment system also includes a control unit that controls the operation of the pressure controller based on the output from the sensing system. More specifically, the control unit causes the pressure of breathing gas to be provided to the patient in accordance with the following relation:

$$P_{patient} = R_1(t)\{[R_2(t)*(\% \text{ Set})]*[((R_3(t)*(FA)(\dot{V})) + (R_4(t)*(VA)(V))] + R_5(t)*EPAP\},$$

where $P_{patient}$ is the pressure at an airway of the patient, % Set is a multiplier, FA is a flow assist multiplier, VA is a volume assist multiplier, EPAP is an expiratory positive airway pressure, and $R_1(t)$, $R_2(t)$, $R_3(t)$, $R_4(t)$, and $R_5(t)$ are time-based parameter variation functions. In addition, at least one of the parameter variation functions $R_1(t)$, $R_2(t)$, $R_3(t)$, $R_4(t)$, and $R_5(t)$ is a function other than a unity function or one (1). By providing these parameter variation functions in the calculation of the pressure to be provided to the patient, the present invention enables one or more of the parameters in the above PAV equation to change over time, rather than subject the patient to an abrupt ventilation change.

In another embodiment of the present invention, the control unit causes the flow of breathing gas to be provided to the patient at a pressure in accordance with a following relation at least during a portion of the breathing cycle:

$$P_{patient} = R_1(t)[R_2(t)\text{Gain}*\dot{V} + R_3(t)P_{base}],$$

where $P_{patient}$ is the pressure at an airway of such a patient, Gain is a constant, $P_{base}$ is a base-line pressure, and $R_1(t)$, $R_2(t)$, and $R_3(t)$ are time-based parameter variation functions, where at least one parameter variation function $R_1(t)$, $R_2(t)$, and $R_3(t)$ is a function other than a unity function or one (1). As in the embodiment discussed above, by providing these parameter variation functions in the calculation of the pressure to be provided to the patient, the present invention enables one or more of the parameters in the above PPAP equation to change over time, rather than subject the patient to an abrupt ventilation change. As described in greater detail below, the present invention also contemplates providing different PPAP equations, with the potential for different parameter variation functions, during the inspiratory and expiratory phases of the breathing cycle, as well as providing PPAP in combination with providing a continuous positive airway pressure (CPAP) or a bi-level positive airway pressure.

It is yet another object of the present invention to provide a method of treating a patient with PAV or PPAP mode of ventilation that does not suffer from the disadvantages associated with conventional PAV or PPAP ventilation techniques. This object is achieved by providing a method that includes providing a flow of breathing gas to an airway of a patient, detecting an instantaneous flow rate $\dot{V}$ and an instantaneous volume V of the flow of breathing gas, and controlling a pressure of breathing gas provided to an airway of the patient in accordance with the following relation:

$$P_{patient} = R_1(t)\{[R_2(t)*(\% \text{ Set})]*[((R_3(t)*(FA)(\dot{V})) + (R_4(t)*(VA)(V))] + R_5(t)*EPAP\},$$

where $P_{patient}$ is the pressure at an airway of the patient, % Set is a multiplier, FA is a flow assist multiplier, VA is a volume assist multiplier, EPAP is an expiratory positive airway pressure, and $R_1(t)$, $R_2(t)$, $R_3(t)$, $R_4(t)$, and $R_5(t)$ are time-based parameter variation functions, where at least one parameter variation function $R_1(t)$, $R_2(t)$, $R_3(t)$, $R_4(t)$, and $R_5(t)$ is a function other than a unity function or one (1).

Still further embodiments of the present invention contemplate using a similar method to provide the PPAP mode of ventilation to the patient, with the parameter variation functions being provided for one or more terms in the PPAP pressure calculation or calculations, depending on whether different PPAP equations are used for inspiration and expiration. As noted above, by providing parameter variation functions in the calculation of the pressure to be provided to the patient, the present invention enables one or more of the parameters in the PAV or PPAP pressure calculation equation to change over time, rather than subject the patient to an abrupt ventilation change.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
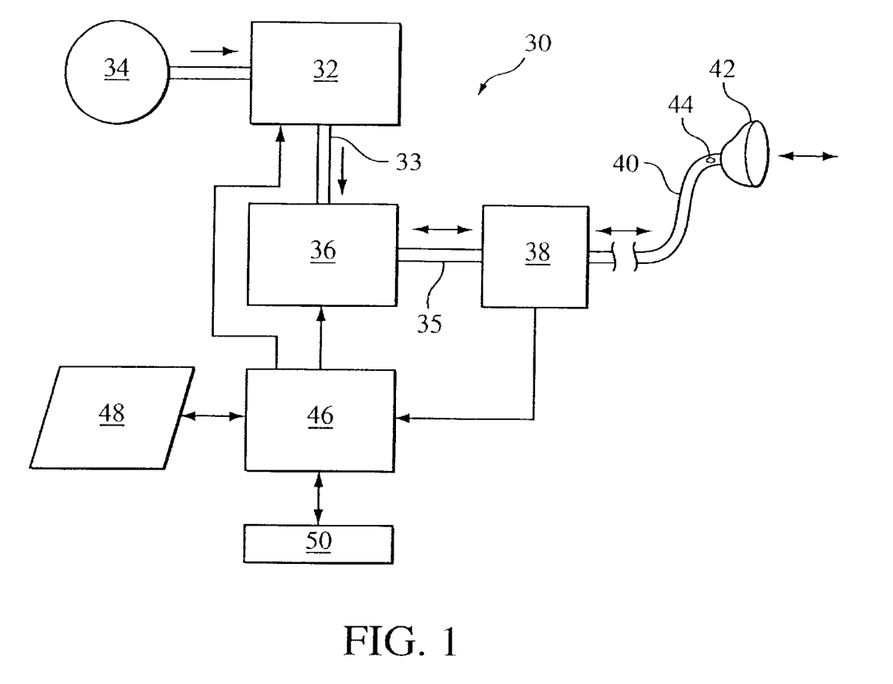
FIG. 1 is a schematic diagram of a first embodiment of pressure support system capable of administering a pressure support treatment according to the principles of the present invention.

FIG. 1 schematically illustrates an exemplary first embodiment of a patient treatment system 30 capable of providing and automatically controlling the pressure of breathing gas delivered to a patient using a PAV or PPAP mode of ventilation according to the principles of the present invention. Patient treatment system 30 includes a pressure generator 32 that receives a supply of breathing from a breathing gas source 34 and elevates the pressure of that gas for delivery to the airway of a patient. Pressure generator 32 is any device, such as a blower, piston, or bellows that is capable of elevating the pressure of the received breathing gas for delivery to a patient. The present invention also contemplates that the pressure generator can be defined by a canister or tank of pressurized gas, with the pressure delivered to the patient being controlled by a pressure regulator.

In one embodiment of the present invention, pressure generator is a blower that is driven at a constant speed during the course of the pressure support treatment to produce a constant pressure or flow rate at its output 33. The present invention contemplates that breathing gas source 34 is any supply of breathing gas, such as ambient atmosphere, a tank of pressurized gas, and an oxygen concentrator. Furthermore, the breathing gas for delivery to the patient can be any gas, such as air or an oxygen mixture, e.g., heliox, or a mixture of a breathing gas and a medication, which can be in gaseous form, such as nitric oxide, or nebulized.

In the illustrated embodiment, the elevated pressure flow of breathing gas from pressure generator 32 is delivered to a control valve 36 downstream of the pressure generator. Control valve 36, either alone or in combination with pressure generator 32, controls the final pressure or flow of gas 35 exiting the pressure/flow generating system, which, in this embodiment includes pressure generator 32 and control valve 36. Examples of a suitable pressure/flow controller includes at least one valve, such as sleeve or poppet valve, that exhausts gas from the patient circuit as a method of controlling the pressure in the patient circuit. U.S. Pat. No. 5,694,923 to Hete et al., the contents of which are incorporated herein by reference, teaches a dual poppet valve system suitable for use as control valve 36 that exhausts gas to atmosphere and restricts the flow of gas from the pressure generator to the patient. Other suitable pressure/flow controllers are believed to be well known to those skilled in the art.

If pressure generator 32 is a blower that operates at all times at only one speed, then control valve 36 alone controls the final pressure and flow rate for the breathing gas 35 delivered to the patient. However, the present invention also contemplates controlling the operating speed of pressure generator 32 in combination with control valve 36 to control the final pressure and flow rate for the breathing gas delivered to the patient. For example, a pressure or flow rate close to the desired pressure or flow rate can be set by establishing an appropriate operating speed for pressure generator 32 (macro control). Fine tuning (micro control) of the pressure or flow rate can then be provided by control valve 36 so that the two, operating together, determine the final pressure for the breathing gas delivered to the patient.

The flow of breathing gas output 35 from control valve 36 is delivered to a sensor 38 to determine the instantaneous volume V of gas delivered to the patient, the instantaneous flow rate $\dot{V}$ of such gas to the patient, or both. Sensor 38 is any device suitable for measuring these parameters, such as a spirometer, pneumotach, variable orifice transducer, or other conventional flow transducer. In the illustrated embodiment, sensor 38 is provided at a location relatively distant from patient interface device. The present invention, however, contemplates locating sensor 38 at any location along patient circuit 40 as well as at patient interface 42. For example, U.S. Pat. No. 6,017,315 to Starr et al., the contents of which are incorporated herein by reference, teaches a quantitative flow member that is located at the patient interface.

The flow of breathing gas is carried to the, patient via a patient circuit 40, which is typically a single flexible conduit that carries the flow of breathing gas to a patient interface device 42. Patient interface device 42 is any appliance, either invasive or non-invasive, such as a nasal mask, nasal/oral mask, total face mask, nasal cannula, endotracheal tube, or tracheal tube, suitable for communicating a supply of breathing gas to the airway of a patient. In the illustrated embodiment, the patient interface device 42 and/or patient circuit 40 includes a suitable exhaust port 44 for exhausting gas from these components to ambient atmosphere. Exhaust port 44 is preferably a passive exhaust port in the form of a continuously open port that imposes a flow restriction on the exhaust gas to permit control of the pressure of gas within patient interface device 42. It is to be understood, however, that exhaust port 42 can be an active exhaust port that assumes different configurations to control the exhaust rate. Examples of suitable exhaust ports are taught, for example, in U.S. Pat. Nos. 5,685,296 and 5,937,855 both to Zdrojkowski et al.

The output of sensor 38 is provided to a control unit 46 for processing, if needed, to determine the instantaneous volume V of gas delivered to the patient, the instantaneous flow rate $\dot{V}$ of such gas to the patient, or both. For example, the instantaneous volume is determined by integrating the measured flow rate. Because the flow sensor is located relatively far from the patient interface in the illustrated embodiment, in order to determine the actual flow rate of gas to the patient or the actuation flow rate of gas from the patient, which is considered a negative flow, control unit 46 receives the output from sensor 38 as an estimated flow and processes this estimated flow information, for example, by performing leak estimation, to determine the actual flow at the patient's airway, as is known to those skilled in the art.

An input/output device 48 provides data and commands to control unit 46 and outputs, in human perceivable form, any information of interest. Input/output device 48 is any device suitable to provide information and/or commands to control unit 46 via a hardwire or wireless connection and to present information to a user in a human perceivable format. Examples of a suitable input/output device includes a keypad, keyboard, touch pad, mouse, visual display (e.g., LCD or LED screen), microphone, speaker, switches, button, dials, lamps, or any other devices that allow a user to input information to and receive information from the treatment system.

The present invention also contemplates that the patient circuit can be a two-limb circuit, which is common in conventional ventilators. The first limb, like patient circuit 40, delivers breathing gas to the patient, except that it lacks an exhaust port. Instead, the second limb carries the exhaust gases from the patient to ambient atmosphere. Typically, an active exhaust port in the second limb under the control of a controller 46 provides the desired level of positive end expiratory pressure PEEP to the patient. In addition, patient circuit 40 and related components can include other conventional devices, such as a humidifier, heater, bacteria filter, temperature sensor, pressure sensor, flow sensor, humidity sensor, and a gas sensor, e.g., a capnometer, that filter, measure, monitor, and analyze the flow of gas to or from the patient.

Control unit 46 controls the actuation of control valve 36, thereby controlling the pressure of the breathing gas delivered to the patient. In accordance with the principles of the present invention, the pressure of the breathing gas is provided to the patient according to the PAV or PPAP modes of ventilation discussed above. Thus, control unit 46 is suitably programmed with the necessary algorithm or algorithms for calculating the pressure to be applied to the patient according to these modes of ventilation. In a more advanced embodiment of the present invention, the control unit includes a memory 50 that stores the programming necessary to perform both PAV and PPAP ventilation, depending on which mode of ventilation is selected by the caregiver using input/output device 48. Of course, memory 50 is also capable of storing data regarding the operation of the patient treatment system, input commands, alarm thresholds, as well as any other information pertinent to the operation of the patient treatment system, such as measured values of patient flow, volume, pressure, device usage, operating temperatures, and motor speed.

Before discussing, in detail, how the present invention provides and controls the pressure of the breathing gas according to the PAV or PPAP modes of ventilation, an alternative embodiment of a patient treatment system 52 is first discussed below with reference to FIG. 2. Unlike patient treatment system 30 of FIG. 1, where the final pressure of the breathing gas delivered to the patient is controlled by control valve 36, either alone or in combination with pressure generator 32, patient treatment system 52 of FIG. 2 controls the pressure of breathing gas delivered to the patient based only on the output of a pressure generator 54. That is, controller 46 controls the pressure of breathing gas delivered to the patient by controlling only the motor speed of pressure generator 54, which is preferably a blower. The present invention contemplates providing, if necessary, ancillary feedback systems, such a pressure monitor in patient circuit 40, motor speed monitor, or pressure generator output monitor that provides feedback data to control unit 46 for controlling the operation of pressure generator 54.

The technique for providing the pressure of the breathing gas according to the PAV or PPAP modes of ventilation and for controlling the pressure provided according to the modes of ventilation using one or more parameter variation functions are now discussed below. According to one embodiment of the present invention in which a PAV mode of ventilation is administered to the patient, control unit 46 causes the flow of breathing gas to be provided to the patient at a pressure in accordance with the following relation:

$$P_{patient}=R_1(t)\{[R_2(t)*(\% \text{ Set})]*[((R_3(t)*(FA)(V))+(R_4(t)*(VA)(V))]+R_5(t)*EPAP\}, \quad (6)$$

where $P_{patient}$ is the pressure at an airway of the patient, % Set is a multiplier, FA is the flow assist multiplier discussed above, VA is the volume assist multiplier discussed above, and EPAP is the expiratory positive airway pressure also discussed above. The functions $R_1(t)$, $R_2(t)$, $R_3(t)$, $R_4(t)$, and $R_5(t)$ are time-based parameter variation functions used to control or change the effective values of % Set, FA, VA, EPAP, or combinations thereof. In accordance with the principles of the present invention, at least one parameter variation function $R_1(t)$, $R_2(t)$, $R_3(t)$, $R_4(t)$, and $R_5(t)$ is a function other than a unity function or one (1).

By providing time-based parameter variation functions $R_1(t)$, $R_2(t)$, $R_3(t)$, $R_4(t)$, and $R_5(t)$, which can be set by the caregiver or preset in advance, the present invention provides a high degree of flexibility for varying the parameters associated with the PAV equation without requiring constant monitoring and manual adjustment by the supervising caregiver. This allows for a very smooth transition into and out of PAV, while minimizing the amount of supervision, monitoring and adjusting required of the caregiver.

A simplified example of the operation of the parameter variation function in providing PAV is discussed below. In this example, the parameter variation functions are defined as follows:

$R_2(t)=\text{Min}\{1.0, 0.1*t+0.2 \text{ per second}\}$, and $R_1(t)$, $R_3(t)$, $R_4(t)$, and $R_5(t)=1$(unity function).

In this example, the parameter variation function $R_1(t)$ starts at 0.2 (t=0) and increases to 1.0 over the next 8 seconds (t=8). The other parameter variation functions $R_2(t)$, $R_3(t)$, and $R_4(t)$ are set to 1 or unity and, thus, do not affect the PAV equation. In this example, if % Set is set to 80%, then the effective % Set, which is defined as $R_1(t) * \%$ Set, starts at 0.2*80%=16% and over the next 8 seconds increases to 1.0*80%=80%. It can be appreciated from this example of the operation of the PAV mode of ventilation that a relative smooth yet rapid transition into the application of PAV ventilation is provided for the patient's comfort.

Figure 3:
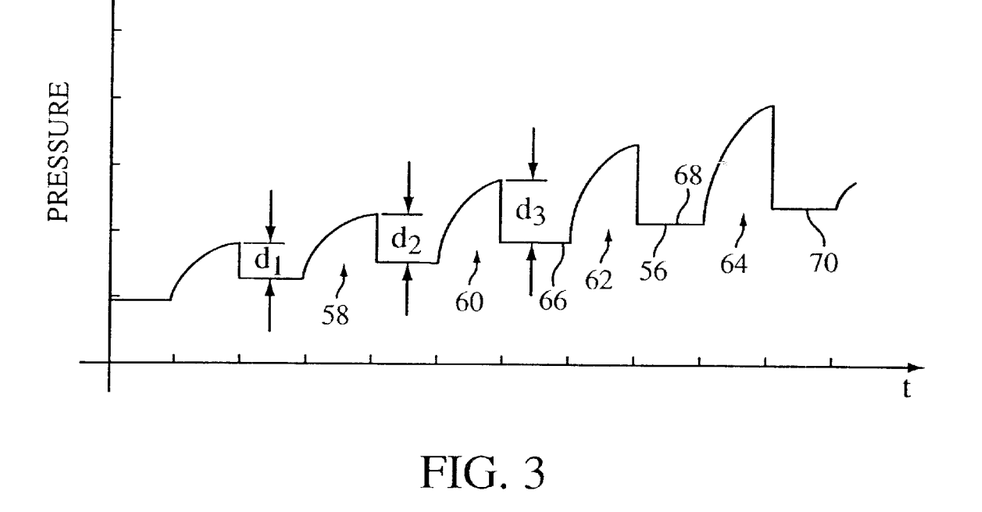
FIG. 3 is a pressure curve illustrating an example of how the PAV pressure provided to the patient can vary over time according to the principles of the present invention.

FIG. 3 shows a pressure curve 56 graphically illustrating how the PAV pressure delivered to the patient varies as a result of a defining parameter variation function $R_1(t)$ as a linear increasing function, such as $R_1(t)=\text{Min}\{1.0, 0.1*t+0.1$ per second$\}$. Because parameter variation function $R_1(t)$ is applied to each term in equation (6), the general shape of curve 56 remains the same as $R_1(t)$ increases, yet the overall size of curve 56 increases in later time increments 58, 60, 62, and 64. For example, in FIG. 3, the distance $d_1$, $d_2$, and $d_3$ increase in subsequent time increments. In addition, the EPAP levels 66, 68 and 70 also increase in later time increments, because, in this situation, $R_1(t)$ is applied to the EPAP level.

Figure 4:
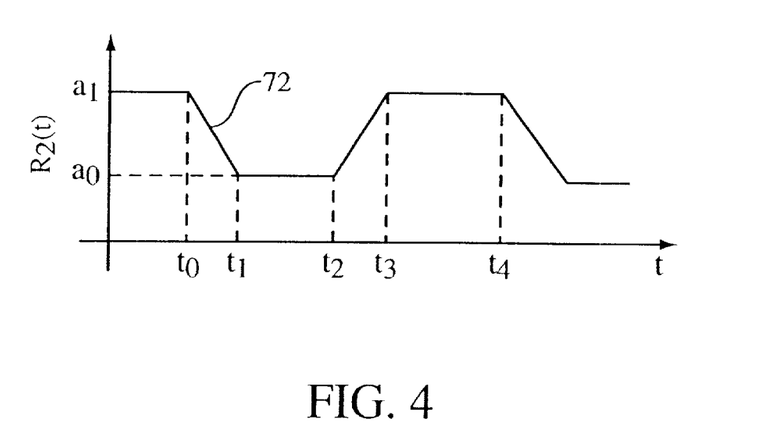
FIG. 4 is a diagram of an exemplary embodiment of a time-based parameter variation function.

FIG. 4 illustrates an exemplary embodiment of a function 72 for parameter variation function $R_2(t)$ that is believed to be useful in weaning a patient off of the PAV mode of ventilation. In this embodiment, the values of $a_0$ and $a_1$ are scaling constants, which, for this example, have a range of zero (0) to one (1), respectively. The weaning activity being at time to, where $R_2(t)$ decreases linearly from $a_1$ to a value of $a_0$ at time $t_1$. $R_2(t)$ is held at $a_0$ a period until time $t_2$, where it increases linearly to $a_1$ again. The time periods $t_0-t_1$, $t_1-t_2$, and $t_2-t_3$ in this weaning cycle can be varied. A similar process can be repeated, beginning at $t_4$, to repeat the above-described weaning exercise, where during time period $t_1-t_2$ the patient receives substantially no assistance other than EPAP pressure to allow the patient to be weaned off of the ventilator support. Of course, the time periods can change over time, for example, the time periods $t_1-t_2$ where the patient receives substantially no assistance can increase as the number of weaning cycles increase.

According to another embodiment of the present invention, a PPAP mode of pressure support ventilation is administered to the patient and controlled according to one or more parameter variation functions. In this embodiment, control unit 46 causes the flow of breathing gas to be delivered to the patient at a pressure in accordance with the following relation:

$$P_{patient}=R_1(t)[R_2(t)\text{Gain}*\dot{V}+R_3(t)P_{base}], \qquad (7)$$

where $P_{patient}$ is the pressure at an airway of the patient, Gain is a constant, $P_{base}$ is a base-line pressure (which can be set to zero), and $R_1(t)$, $R_2(t)$, and $R_3(t)$ are time-based parameter variation functions. As with the previous embodiment, at least one of the parameter variation functions $R_1(t)$, $R_2(t)$, and $R_3(t)$ is a function other than a unity function. By providing parameter variation functions $R_1(t)$, $R_2(t)$, and $R_3(t)$ in the calculation of the PPAP pressure to be provided to the patient, the present invention enables one or more of the parameters in the PPAP pressure calculation equation to change over time, rather than subject the patient to an abrupt ventilation change, thereby optimizing the patient's comfort.

In the above described PPAP embodiment, the same gain is applied to the flow during inspiration and expiration. However, it may be desirable to apply different gains to the flow during each of these phases of the patient's breathing cycle. To this end, the present invention contemplates that control unit 46 controls the pressure of breathing gas delivered to the patient in accordance with the relation of equation (7) during patient inspiration or during an inspiratory cycle of the pressure support system, and in accordance with a following relation during patient exhalation or during an expiratory cycle of the pressure support system:

$$P_{patient}=R_4(t)[R_5(t)\text{Gain}_{exp}*\dot{V}+R_6(t)P_{base}], \qquad (8)$$

where $R_4(t)$, $R_5(t)$, and $R_6(t)$ are time-based parameter variation functions. At least one parameter variation function $R_4(t)$, $R_5(t)$, and $R_6(t)$ is a function other than a unity function. $P_{base}$ in equation (8) can be the same as or different from $P_{base}$ in equation (7), and either or both can be set to zero depending on the desired operating characteristics of the PPAP system.

In short, the present invention contemplates using the following PPAP relations to set the pressure delivered to the patient:

$$P_{patient(insp)}=R_1(t)[R_2(t)\text{Gain}_{insp}*\dot{V}+R_3(t)P_{base}], \text{ and} \qquad (9)$$

$$P_{patient(exp)}=R_4(t)[R_5(t)\text{Gain}_{exp}*\dot{V}+R_6(t)P_{base}]. \qquad (10)$$

wherein $P_{patient(insp)}$ is the PPAP relation used during inspiration or during an inspiratory cycle of the pressure support system, and $P_{patient(exp)}$ is the PPAP relation used during expiration or during an expiratory cycle of the pressure support system.

Determining when the patient is in the inspiratory and expiratory phases is accomplished using any conventional technique, such as by monitoring the gas flow or pressure at the patient's airway or monitoring the expansion of the patient's chest. Likewise, triggering and cycling the pressure support system between the inspiratory and expiratory operating cycles, so that the appropriate PPAP relation is used in each cycle, is also accomplished by any conventional technique, such as by monitoring the sign (positive or negative) of the flow of gas at the patient's airway, monitoring the shape of a signal corresponding to such flow, or by comparing flow signal to another signal, such as a threshold valve.

Figure 2:
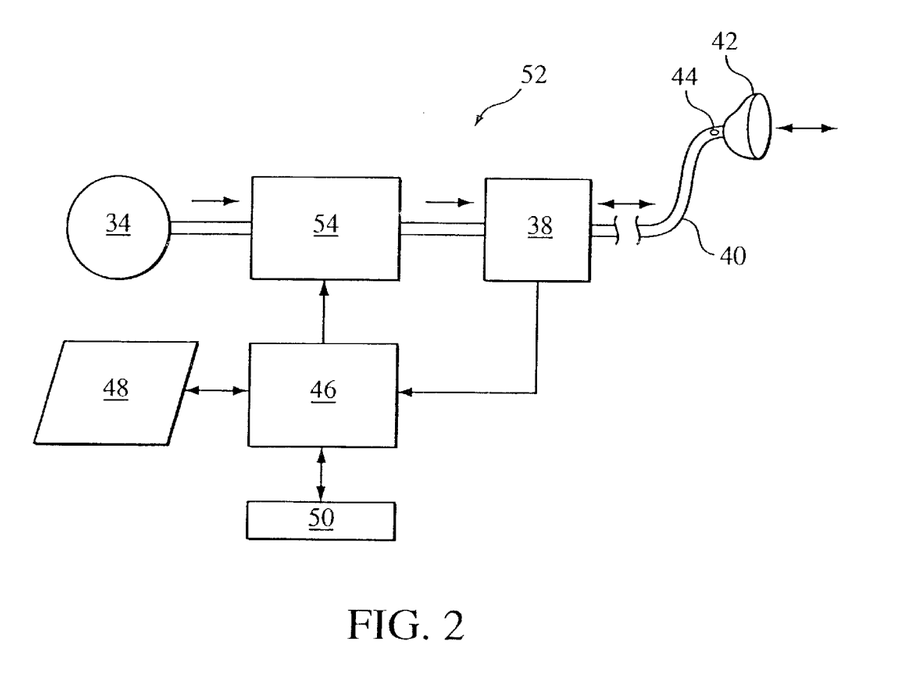
FIG. 2 is a schematic diagram of a second embodiment of pressure support system capable of administering a pressure support treatment according to the principles of the present invention.
Figure 5A:
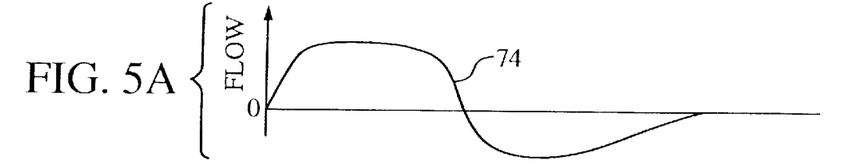
FIGS. 5A–5B, 6A–6B, and 7A–7B illustrate exemplary output flow and PPAP pressure curves that can be provided by the patient treatment systems of FIGS. 1 or 2 and further show how the PPAP pressure provided to the patient can vary over time according to the parameter variation functions of the present invention.
Figure 5B:
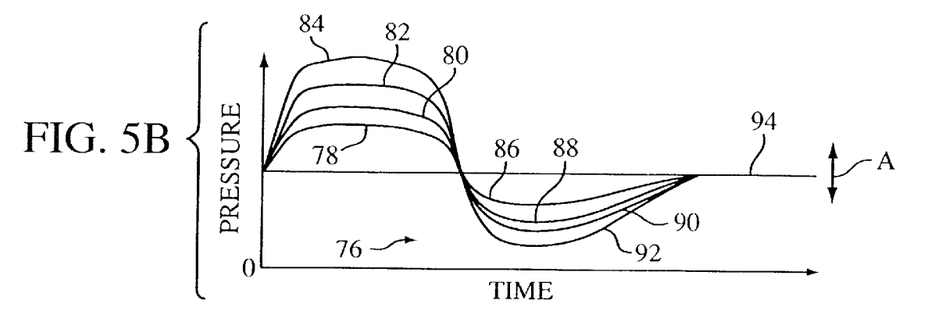

FIGS. 5A and 5B illustrate a flow curve 74 and pressure curves 76 that can be provided by the above-described device shown in FIGS. 1 and 2 as the $\text{Gain}_{insp}$ and $\text{Gain}_{exp}$ are adjusted according to the parameter variation functions. Pressure curve 78 illustrates $\text{Gain}_{insp}$ set to a first predetermined level. Pressure curves 80, 82 and 84 illustrate how the inspiratory portion of the pressure curve changes as a result of linearly increasing $\text{Gain}_{insp}$ over successive time increments, i.e., $R_2(t)=\text{Min}\{1.0, 0.1*t+0.1 \text{ per second}\}$. Similarly, pressure curve 86 illustrates $\text{Gain}_{exp}$, set to a first predetermined level, and pressure curves 88, 90 and 92 illustrate how the inspiratory portion of the pressure curve changes as a result of linearly increasing $\text{Gain}_{exp}$ over successive time increments. It should also be noted that base pressure $P_{base}$ 94 can be increased or decreased, as indicated by arrow A, in addition to or in place of the changes in $\text{Gain}_{insp}$ and $\text{Gain}_{exp}$, over successive respiratory cycles.

Additional embodiments for providing PPAP to a patient include providing PPAP in combination with providing continuous positive airway pressure (CPAP) or in combination with bi-level pressure support, where a higher pressure is applied to the patient during inspiration than during expiration, so that a portion of the pressure profile is provided to the patient in accordance with a PPAP technique and another portion of the pressure profile is provided in accordance with a CPAP or bi-level pressure support technique. Of course, in the bi-level pressure support mode, controller 46 includes the necessary circuits and/or programming to effect the bi-level pressure control, including, for example, breathing cycle triggering and leak compensation/estimation.

Figure 6A:
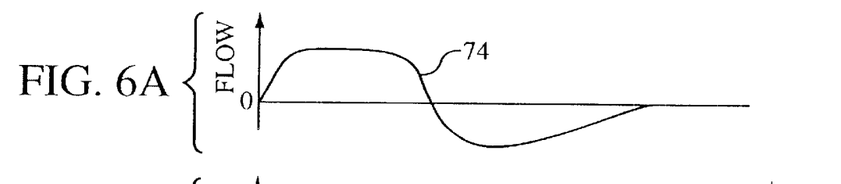
Figure 6B:
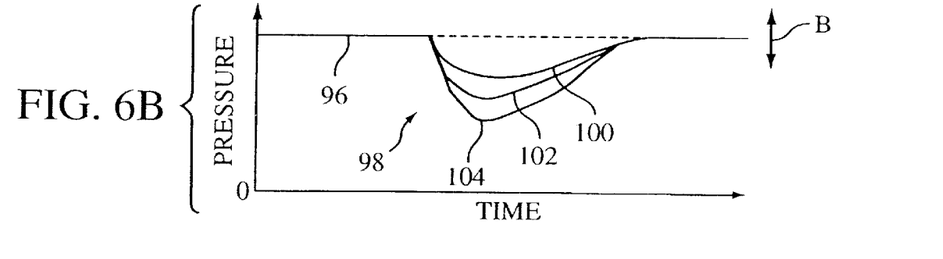

FIGS. 6A and 6B are exemplary flow and pressure curves, respectively, showing an example of the use of PPAP control, which is provided in accordance with equation (7), in conjunction with CPAP 96. In this embodiment, PPAP control is only used during the expiratory phase of the breathing cycle. It can be appreciated, however, that PPAP control can be used at other portions of the respiratory cycle, with CPAP control being used whenever PPAP control is not applied. It can be noted that the same result can be achieved using equations (9) and (10) if $R_1(t)=1$, $R_2(t)=0$, and $R_3(t)=1$, effectively making equation (9) equal to $P_{base}$, which is effectively equal to CPAP.

As shown in FIG. 6B, using PPAP control only during the expiratory phase results in a decrease in pressure delivered to the patient as illustrated by pressure curves 98 during the expiratory phase. Pressure curve 100 illustrates $\text{Gain}_{exp}$ set to a first predetermined level, and pressure curves 102 and 104 illustrate how the expiratory portion of the pressure curve can be changed as a result of linearly increasing $\text{Gain}_{exp}$ over successive time increments by, for example, by setting $R_5(t)$ to a linearly increasing function. CPAP level 96 can be increased or decreased, as indicated by arrow B, over successive time increments in addition to or in place of the changes in $\text{Gain}_{insp}$ and $\text{Gain}_{exp}$ by providing a parameter variation function associated with the CPAP pressure level.

Figure 7A:
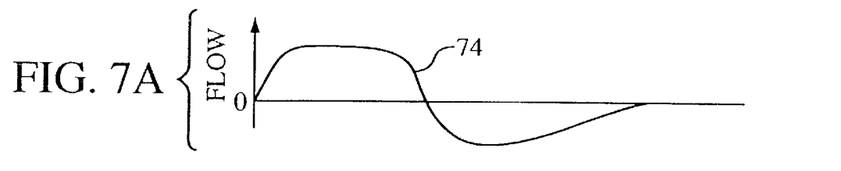
Figure 7B:
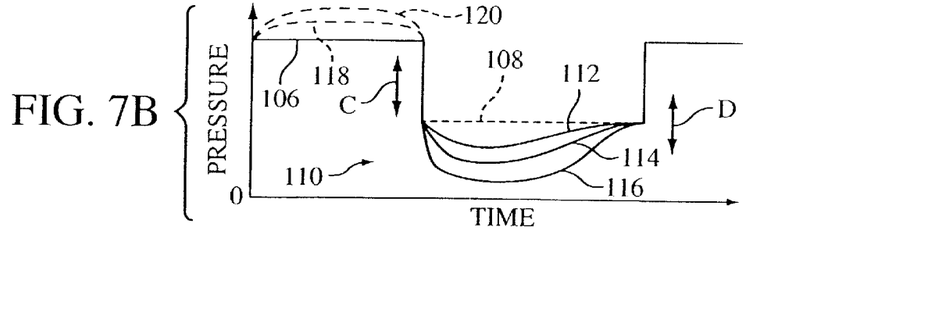

FIGS. 7A and 7B are flow and pressure curves, respectively, showing an example of the use of PPAP control in combination with bi-level pressure control. As shown in FIG. 7B, an inspiratory positive airway pressure (IPAP) 106 is delivered during inspiration, and an EPAP 108 is delivered during expiration. In this embodiment, PPAP control is only used during the expiratory phase. It can be appreciated, however, that PPAP control can also be used only during the inspiratory phase or during both inspiratory and expiratory phases of the breathing cycle.

As shown in FIG. 7B, providing PPAP control in combination with bi-level control during the expiratory phase results in a decrease in pressure of gas administered to the patient, as illustrated by pressure curves 110, during the expiratory phase. Pressure curve 112 illustrates $Gain_{exp}$ set to a first predetermined level, and pressure curves 114 and 116 illustrate how the expiratory portion of the pressure curve changes as a result of increasing $Gain_{exp}$ over successive time increments by providing, for example, a linearly increasing parameter variation function $R_5(t)$ associated with the $Gain_{exp}$. IPAP level 106 and EPAP level 108 can be increased or decreased, as indicated by arrows C and D, respectively, over successive respiratory cycles in addition to or in place of the changes in $Gain_{insp}$ and $Gain_{exp}$. Dashed lines 118 and 120 illustrate how the pressure curve would look during inspiration if PPAP control is used in combination with IPAP during the inspiratory phase. $Gain_{insp}$ in pressure curve 120 is greater than $Gain_{insp}$, in pressure curve 118.

It is also known to use PPAP in conjunction with a predetermined pressure profile so that a portion of the pressure output follows a preset pressure profile. The PPAP portion of the pressure output, which is provided in accordance with equation (7) or in accordance with equations (9) and (10), can be controlled according to one or more parameter variation functions as discussed above.

From the above examples, those skilled in the art can appreciate how the use of a parameter variation function associated with the terms or group of terms in the PAV or PPAP equations provides a high degree of flexibility in transitioning between various pressure outputs, for example, upon start-up or termination of the PAV or PPAP therapy. Furthermore, present invention contemplates a potentially infinite variety of shapes, contours, and variations for the parameter variation functions $R_1(t)$, $R_2(t)$, $R_3(t)$, $R_4(t)$, $R_5(t)$, and $R_6(t)$ used in equations (6)–(10). For example, one or more of the parameter variation functions can be expressed as a linear ramp, trapezoid, triangle, square wave, sinusoidal, exponential, or other function. Furthermore, the parameter variation function can be determined from a polynomial equation or from a graphically entered functions, such as that shown in FIG. 3. In addition, the various parameter variations functions can be related to or dependent upon one another or completely independent of one another.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient treatment system comprising:

gas flow generating means for providing a flow of breathing gas to an airway of a patient;

pressure controlling means, associated with the gas flow generating means, for controlling a pressure of breathing gas provided to an airway of such a patient;

sensing means for detecting an instantaneous flow rate V and an instantaneous volume V of the flow of breathing gas provided to such a patient; and processing means, associated with the sensing means and the pressure controlling means, for controlling the pressure controlling means such that the flow of breathing gas is provided to such a patient at a pressure in accordance with the following relation:

$$P_{patient} = R_1(t)\{[R_2(t)*(\% \text{ Set})]*[(R_3(t)*(FA)(\dot{V})) + (R_4(t)*(VA)(V))] + R_5(t)*EPAP\},$$

where $P_{patient}$ is the pressure at an airway of such a patient, % Set is a multiplier, FA is a flow assist multiplier, VA is a volume assist multiplier, EPAP is an expiratory positive airway pressure, and $R_1(t)$, $R_2(t)$, $R_3(t)$, $R_4(t)$, and $R_5(t)$ are time-based parameter variation functions, and where at least one parameter variation function $R_1(t)$, $R_2(t)$, $R_3(t)$, $R_4(t)$, and $R_5(t)$ is a function other than a unity function.

2. A system according to claim 1, wherein parameter variation functions $R_1(t)$, $R_2(t)$, $R_3(t)$, $R_4(t)$, and $R_5(t)$ are independent of one another.

3. A system according to claim 1, wherein the gas flow generating means comprises:

a blower that receives a supply of breathing gas an elevates a pressure of such gas and output a flow of breathing gas;

a patient circuit having a first end coupled to the blower and a second end, wherein the patient circuit carries the flow of breathing gas; and a patient interface coupled to the second end of the patient circuit to communicate the flow of breathing gas from the patient circuit to an airway of a patient, and wherein the pressure controlling means comprises at least one of:

(a) a control valve coupled to the patient circuit that controls a pressure of flow of breathing gas delivered to a patient by at least one of exhausting gas from the patient circuit and restricting the flow of breathing gas in the patient circuit; and (b) a variable speed motor coupled to the blower that controls a pressure of the flow of breathing gas delivered to a patient by controlling a rotational velocity of the blower, and, hence, a pressure of the flow of breathing gas output by the blower.

4. A system according to claim 1, further comprising an input/output means for setting at least one of the % Set, FA, VA, EPAP, $R_1(t)$, $R_2(t)$, $R_3(t)$, $R_4(t)$, and $R_5(t)$.

5. A system according to claim 1, further comprising a memory for storing information regarding at least one of the % Set, FA, VA, EPAP, $R_1(t)$, $R_2(t)$, $R_3(t)$, $R_4(t)$, and $R_5(t)$.

6. A method of treating a patient comprising:

providing a flow of breathing gas to an airway of a patient;

detecting an instantaneous flow rate $\dot{V}$ and an instantaneous volume V of the flow of breathing gas provided to such a patient; and controlling a pressure of breathing gas provided to an airway of such a patient in accordance with the following relation:

$$P_{patient} = R_1(t)\{[R_2(t)*(\% \text{ Set})]*[(R_3(t)*(FA)(\dot{V})) + (R_4(t)*(VA)(V))] + R_5(t)*EPAP\},$$

where $P_{patient}$ is the pressure at an airway of such a patient, % Set is a multiplier, FA is a flow assist multiplier, VA is a volume assist multiplier, EPAP is an expiratory positive airway pressure, and $R_1(t)$, $R_2(t)$, $R_3(t)$, $R_4(t)$, and $R_5(t)$ are time-based parameter variation functions, and where at least one parameter variation function $R_1(t)$, $R_2(t)$, $R_3(t)$, $R_4(t)$, and $R_5(t)$ is a function other than a unity function.

7. A method according to claim 6, further comprising setting parameter variation functions $R_1(t)$, $R_2(t)$, $R_3(t)$, $R_4(t)$, and $R_5(t)$ independent of one another.

8. A method according to claim 6, wherein providing a flow of breathing gas to an airway of a patient includes:

generating the flow of breathing gas via a blower;

carrying the flow of breathing gas to a patient via a patient circuit having a first end coupled to the blower and a second end; and communicating the flow of breathing gas to an airway of such a patient via a patient interface coupled to the second end of the patient circuit, and wherein controlling the pressure of the breathing gas provided to the patient includes least one of:

(a) exhausting gas from the patient circuit, (b) restricting the flow of breathing gas in the patient circuit, and (c) controlling a rotational velocity of the blower, and, hence, a pressure of the flow of breathing gas output by the blower.

9. A method according to claim 6, further comprising setting at least one of the % Set, FA, VA, EPAP, $R_1(t)$, $R_2(t)$, $R_3(t)$, $R_4(t)$, and $R_5(t)$ using an input/out device.

10. A method according to claim 6, further comprising storing in a memory information regarding at least one of the % Set, FA, VA, EPAP, $R_1(t)$, $R_2(t)$, $R_3(t)$, $R_4(t)$, and $R_5(t)$.

* * * * *